United States Patent
Funada et al.

(10) Patent No.: US 9,920,346 B2
(45) Date of Patent: Mar. 20, 2018

(54) METHOD OF PREPARING SUGAR SOLUTION

(71) Applicant: Toray Industries, Inc., Tokyo (JP)

(72) Inventors: Shigeyuki Funada, Kamakura (JP); Hiroyuki Kurihara, Kamakura (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 15/513,615

(22) PCT Filed: Sep. 18, 2015

(86) PCT No.: PCT/JP2015/076663
§ 371 (c)(1),
(2) Date: Mar. 23, 2017

(87) PCT Pub. No.: WO2016/047589
PCT Pub. Date: Mar. 31, 2016

(65) Prior Publication Data
US 2017/0306372 A1    Oct. 26, 2017

(30) Foreign Application Priority Data
Sep. 26, 2014 (JP) .................................. 2014-196223

(51) Int. Cl.
*C12N 9/24* (2006.01)
*C12P 7/02* (2006.01)
*C12P 19/14* (2006.01)
*C12P 19/02* (2006.01)

(52) U.S. Cl.
CPC .............. *C12P 19/14* (2013.01); *C12P 19/02* (2013.01); *C12Y 302/01004* (2013.01); *C12Y 302/01008* (2013.01)

(58) Field of Classification Search
CPC ..................................................... C12P 7/02
See application file for complete search history.

(56) References Cited

FOREIGN PATENT DOCUMENTS

| JP | 63-87994 A | 4/1988 |
|---|---|---|
| JP | 9-140379 A | 6/1997 |
| JP | 3041380 B2 | 5/2000 |
| JP | 2006-087319 A | 4/2006 |
| WO | 02/18561 A2 | 3/2002 |
| WO | 2011/115040 A1 | 9/2011 |
| WO | 2015/099109 A1 | 7/2015 |

OTHER PUBLICATIONS

A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report, Jun. 2002.
Pablo Alivra et al., "Strategies of Xylanase Supplementation for an efficient Saccharification and Cofermentation Process from Pretreated Wheat Straw," Biotechnol. Prog., vol. 27, No. 4, 2011, pp. 944-950.
Miyuki Kurosawa et al., "Strategies for Reduction of Enzyme Cost: Development of an Integrated System for Ethanol Production from Herbaceous Biomass by the Consortium of Six Companies and the Univeristy of Tokyo (4)," Biomass Kagaku Kaigi Happyo Ronbunshu, vol. 7, 2012, pp. 122-123 (Abstract only).
H. Kurihara et al., "Development of Novel Sugar Production Processes from Non-edible Biomass by Using Membrane and Enzyme Technologies", 95$^{th}$ Annual Meeting of the Chemical Society of Japan in Spring (2015) Koen Yokoshu II, CSJ: The Chemical Society of Japan, Mar. 11, 2015 (Mar. 11, 2015), p. 216 along with an English abstract. Japanese.
Tatsuya Fujii, "Strain Improvement of Cellulase Hyper-Producing Fungus Acremonium Cellulolyticus: For Developing Biomass Refinery Technology", *Bioscience & Industry*, Jul. 1, 2012, (Jul. 1, 2012), 70 (4), pp. 259 to 262, along with English abstract.

*Primary Examiner* — Maryam Monshipouri
(74) *Attorney, Agent, or Firm* — DLA Piper LLP (US)

(57) ABSTRACT

A method prepares a sugar solution from cellulose-containing biomass. The method includes step (1): a step of obtaining an endoxylanase hydrolysate by hydrolyzing the cellulose-containing biomass using endoxylanase derived from microorganisms of the *Acremonium* genus or the *Aspergillus* genus, step (2): a step of separating the endoxylanase hydrolysate into an endoxylanase hydrolysate solid and an endoxylanase hydrolysate liquid through solid-liquid separation, step (3): a step of obtaining a cellulase hydrolysate by hydrolyzing the endoxylanase hydrolysate solid using cellulase derived from a filamentous fungus, and step (4): a step of filtering the cellulase hydrolysate through an ultrafiltration membrane to recover a sugar solution from the filtrate side and collect an enzyme component from the non-filtrate side.

20 Claims, 2 Drawing Sheets

METHOD OF PREPARING SUGAR SOLUTION

TECHNICAL FIELD

This disclosure relates to a method of producing, from biomass, sugar liquids usable as fermentation feedstocks and the like.

BACKGROUND

The process of fermentation production of chemical products using sugars as raw materials has been used to produce various industrial materials. At present, as the sugars to be used as fermentation feedstocks, those derived from food materials such as sugar cane, starch, and sugar beet are industrially used. However, in view of the fact that increases in the price of food materials is expected due to future increases in the world population, or in an ethical view of the fact that those sugars compete with sugars for food, a process of efficiently producing a sugar liquid from a renewable nonfood resource, that is, cellulose-containing biomass, or a process of using an obtained sugar liquid as a fermentation feedstock to efficiently convert it to an industrial material, needs to be constructed in the future.

As a method of producing a sugar liquid from cellulose-containing biomass, a method of producing a sugar liquid by hydrolysis of cellulose-containing biomass using dilute sulfuric acid followed further by saccharification using an enzyme such as cellulase, as well as a method of producing a sugar liquid by hydrolysis of cellulose and hemicellulose with acid using concentrated sulfuric acid, is known (A. Aden et al., "Lignocellulosic Biomass to Ethanol Process Design and Economics Utilizing Co-Current Dilute Acid Prehydrolysis and Enzymatic Hydrolysis for Corn Stover," NREL Technical report (2002)). A method of producing a sugar liquid by hydrolysis of cellulose-containing biomass with hot compressed water at 240 to 280° C. followed further by saccharification using a saccharifying enzyme is also disclosed (JP 3041380 B2). Among them, in recent years, methods of hydrolysis of biomass using a saccharifying enzyme, which methods use less energy and cause less environmental load but produce sugar at high yields, have been extensively studied. However, methods of producing a sugar liquid using a saccharifying enzyme result in high cost of production of a sugar liquid as the cost of the enzyme is high.

As a means of solving the above-mentioned technical problem in methods of producing a sugar liquid using a saccharifying enzyme, a method of recovering and reusing a saccharifying enzyme which has been used for hydrolysis has been proposed. For example, disclosed are a method in which an enzyme is recovered by filtering, through an ultrafiltration membrane, the sugar liquid obtained by continuous solid-liquid separation through a spin filter (JP 2006-87319 A), a method in which addition of a surfactant at the stage of saccharification of an enzyme suppresses adsorption of the enzyme and enhances the recovery efficiency of the enzyme (JP 63-87994 A) and the like. Also disclosed are a method in which hydrolysis of biomass using the recovered enzyme prior to the next and later saccharification reactions can enhance the recovery efficiency of the enzyme at the saccharification reactions and reduce the amount of enzyme used (WO 2011/115040) and other methods. In WO '040, the recovered enzyme in the Examples is the same filamentous fungus-derived enzyme as the enzyme used for the saccharification reaction, and *Trichoderma* is used in the Examples.

As above-mentioned, a method of recovering the enzyme used for hydrolysis of cellulose-containing biomass has been developed, but its effect is still insufficient in view of reduction of the amount of a saccharifying enzyme used, and a method of producing a sugar liquid with more effective usage of a saccharifying enzyme in producing a sugar liquid from cellulose-containing biomass is demanded.

Accordingly, it could be helpful to provide a method of producing a sugar liquid that can further enhance the effect of reduction in the amount of a saccharifying enzyme used.

SUMMARY

We thus provide:

[1] A method of producing a sugar liquid from a cellulose-containing biomass, comprising:
  Step (1): a step of obtaining an endoxylanase hydrolysate by hydrolyzing the cellulose-containing biomass using endoxylanase derived from microorganisms of the *Acremonium* genus or the *Aspergillus* genus,
  Step (2): a step of separating the endoxylanase hydrolysate into an endoxylanase hydrolysate solid and an endoxylanase hydrolysate liquid through solid-liquid separation,
  Step (3): a step of obtaining a cellulase hydrolysate by hydrolyzing the endoxylanase hydrolysate solid using cellulase derived from a filamentous fungus, and
  Step (4): a step of filtering the cellulase hydrolysate through an ultrafiltration membrane to recover a sugar liquid from the permeate side and recover an enzyme component from the non-permeate side.

[2] The method of producing a sugar liquid according to (1), wherein the cellulose-containing biomass is pretreated by one or more methods selected from the group consisting of alkali treatment, hydrothermal treatment, and dilute sulfuric acid treatment.

[3] The method of producing a sugar liquid according to (1) or (2), wherein an enzyme activity of the endoxylanase is 80 U/mg-protein or more.

[4] The method of producing a sugar liquid according to any one of (1) to (3), wherein the solid-liquid separation of the endoxylanase hydrolysate satisfies the following relational expression:

$$\text{weight of endoxylanase hydrolysate solid} < \text{weight of endoxylanase hydrolysate liquid.}$$

[5] The method of producing a sugar liquid according to any one of (1) to (4), further comprising a step of filtering the endoxylanase hydrolysate liquid through an ultrafiltration membrane to recover a xylooligosaccharide liquid from the permeate side and recover an endoxylanase from the non-permeate side.

[6] The method of producing a sugar liquid according to any one of (1) to (5), wherein the filamentous fungus-derived cellulase is derived from a microorganism(s) belonging to the genus *Trichoderma*.

[7] The method of producing a sugar liquid according to any one of (1) to (6), wherein Step (4) is a step of filtering, through an ultrafiltration membrane, the cellulase hydrolysate liquid obtained by solid-liquid separation of the cellulase hydrolysate, to recover a sugar liquid from the permeate side and recover an enzyme component from the non-permeate side.

[8] The method of producing a sugar liquid according to any one of (1) to (7), wherein the enzyme component is used as the filamentous fungus-derived cellulase in Step (3).

An endoxylanase hydrolysate solid is thus obtained by solid-liquid separation of the endoxylanase hydrolysate obtained by hydrolysis of a cellulose-containing biomass with endoxylanase prior to a saccharification reaction of the cellulose-containing biomass. Recovering and reusing the non-permeate obtained by hydrolysis of this endoxylanase hydrolysate solid with a filamentous fungus-derived cellulase can further enhance the effect of reduction in the amount of a saccharifying enzyme used in production processes of a sugar liquid. This can keep the production costs of a sugar liquid low.

DETAILED DESCRIPTION

Figure 1:
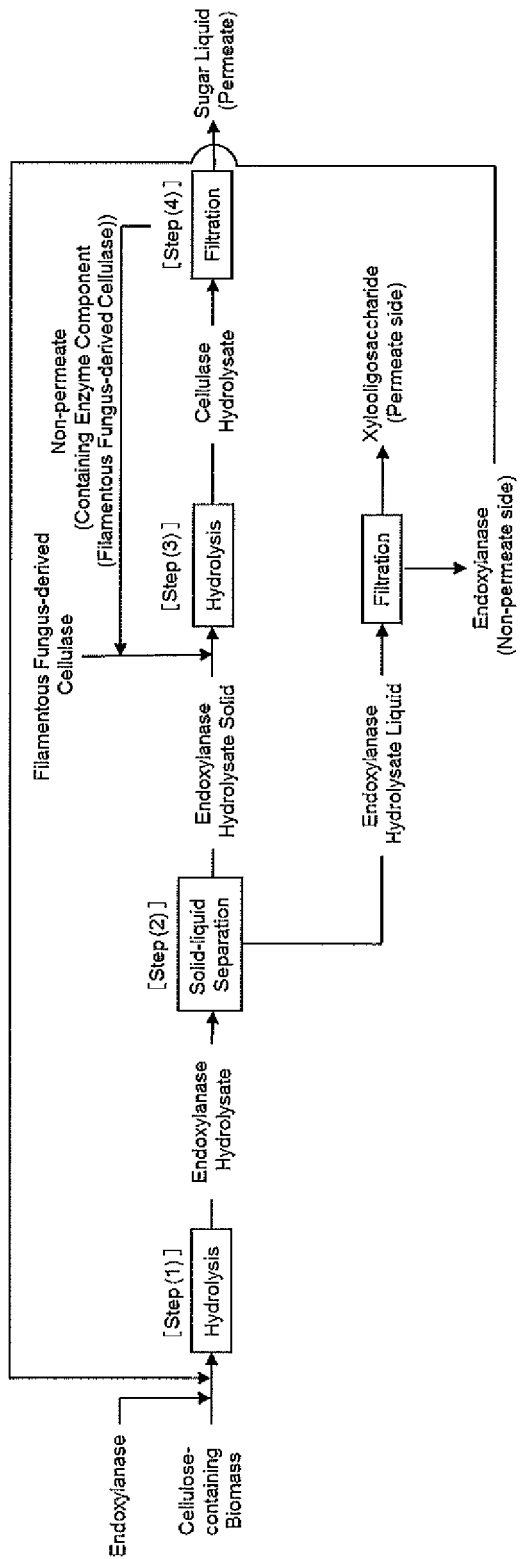
FIG. 1 is a view showing our method of producing a sugar liquid.

A method of producing a sugar liquid is shown in FIG. 1. Our methods will be described step by step in detail and this disclosure is not limited to the following.

Step (1)

Step (1) is a step of obtaining an endoxylanase hydrolysate by hydrolyzing cellulose-containing biomass using endoxylanase derived from microorganisms of the *Acremonium* genus or the *Aspergillus* genus.

The cellulose-containing biomass used in Step (1) refers to a biological resource containing at least cellulose. Specific examples of cellulose-containing biomass include: herbaceous biomasses such as bagasse, corn cob, switchgrass, napier grass, *Erianthus*, corn stover, rice straw, and wheat straw; woody biomasses such as trees and waste building materials; pulp obtained from woody biomass; even water environment-derived biomasses such as algae and sea grasses; or grain hulls biomasses such as corn hulls, wheat hulls, soybean hulls, and rice hulls; and grain hulls biomass and rice straw are most effective and preferably used.

The hydrolysis of cellulose-containing biomass aims at making the molecular weight of cellulose or hemicellulose lower, thereby producing a monosaccharide or oligosaccharide. In the hydrolysis of cellulose-containing biomass with endoxylanase in this Step, xylan which is a hemicellulose component is hydrolyzed. "Endoxylanase is an enzyme which hydrolyzes hemicellulose by acting on a β-1,4-bound xylose backbone, and it is an enzyme classified as EC number: EC 3.3.1.8.

Preferably, cellulose-containing biomass is pretreated prior to hydrolysis of the cellulose-containing biomass with endoxylanase to enhance the efficiency of hydrolysis. This can enhance the efficiency of hydrolysis of cellulose-containing biomass with filamentous fungus-derived cellulase. To prepare for Step (1), a pretreated material of biomass having undergone pretreatment in advance may be purchased, and our methods encompass such an aspect.

Examples of methods of pretreatment of cellulose-containing biomass are not particularly limited, specifically including acid treatment, sulfuric acid treatment, dilute sulfuric acid treatment, alkaline treatment, caustic soda treatment, ammonia treatment, hydrothermal treatment, subcritical water treatment, pulverization treatment, and steaming treatment, and in view of efficiently recovering various enzymes in Step (4) described below, hydrothermal treatment, dilute sulfuric acid treatment, an alkaline treatment are preferred. In hydrothermal treatment, water is added to a biomass solid such that the solid has a concentration of 0.1 to 50 wt %, followed by treatment at a temperature of 100 to 400° C. for 1 to 60 minutes. Treatment under such temperature conditions causes hydrolysis of cellulose or hemicellulose. In particular, the temperature is preferably 100° C. to 250° C., and the treatment time is preferably 5 to 30 minutes. The number of times of treatment is not particularly limited, and such treatment may be performed one or more times. In particular, when such treatment is performed two or more times, the first treatment and the subsequent treatment(s) may be performed under different conditions. Dilute sulfuric acid treatment refers to a treatment in which sulfuric acid is added in hydrothermal treatment. The amount of sulfuric acid to be added is preferably 0.1 to 150 mg per g by weight of cellulose-containing biomass. Alkaline treatment refers to a treatment in which 0.1 to 150 mg of alkali per g by weight of cellulose-containing biomass is added at room temperature or in hydrothermal treatment. As alkali for use, sodium hydroxide, calcium hydroxide, ammonia, or the like can be used. After the pretreatment, the acid and alkali may also be removed through solid-liquid separation.

In this step, endoxylanase derived from microorganisms of the *Acremonium* genus or the *Aspergillus* genus is used for hydrolysis. The endoxylanase may be an enzyme having been purified through a column or the like from a culture liquid which has been cultivated for a certain period of time to produce endoxylanase, or may be obtained by preparing DNA that codes the amino acid sequence of endoxylanase, linking it to an expression vector, introducing the expression vector into a host, producing a protein from a different species or from the same species, and carrying out isolation and purification. The codon usage for coding the amino acid sequence may be the same as for the *Acremonium* or the *Aspergillus*, or may be varied according to the codon usage of the host.

The *Acremonium* genus includes, but not limited to, *Acremonium alternatum, Acremonium curvulum, Acremonium persicinum, Acremonium recifei, Acremonium strictum, Acremonium cellulolyticus* and the like.

The *Aspergillus* genus includes, but not limited to, *Aspergillus aculeatus, Aspergillus clavatus, Aspergillus niger,* and *Aspergillus oryzae.*

Endoxylanase from the *Acremonium* genus is not particularly limited as long as it contains endoxylanase, and includes a purified enzyme into which endoxylanase is purified from "*Acremonium* cellulase" commercially available from Meiji Seika Pharma Co., Ltd. Endoxylanase from the *Aspergillus* genus is not particularly limited as long as it contains endoxylanase, and includes "Cellulosin HC100" commercially available from HBI Enzymes Inc. and the like.

For the activity of endoxylanase, the amount of enzyme that produces 1 μmol of xylose per minute is defined as 1 U, using Birchwood xylan as a substrate. In measurement of the activity, the dinitrosalicylic acid method (DNS method) is used to measure absorbance at 540 nm, thereby measuring the amount of a reducing sugar contained in a reaction liquid after the reaction and allowing the amount of the reducing sugar to be determined relative to a calibration curve previously determined using a known xylose. The conditions for measurement of the activity are determined from a reaction under 1% Birchwood xylan at 50° C. at pH 5 for 10 minutes.

The reaction conditions for hydrolysis by endoxylanase are not limited as long as it is performed according to the preferable reaction conditions of endoxylanase, while as the activity of endoxylanase, a higher activity of xylanase is preferably used because a lower activity increases the amount of endoxylanase added and adversely affects economy. Specifically, endoxylanase of 80 U or more per mg by weight of enzyme is preferable, and endoxylanase of 80 to 100,000 U or more per mg by weight of enzyme is more preferable.

The amount of endoxylanase added is not particularly limited, and 0.05 mg or more of endoxylanase per mg by weight of biomass is preferably added, and 0.1 mg or more is more preferably added. The reaction time of hydrolysis with the addition of endoxylanase is not particularly limited, and is preferably 1 to 48 hours, more preferably 4 to 24 hours. The general reaction temperature in using endoxylanase derived from microorganisms of the *Acremonium* genus or the *Aspergillus* genus is preferably 15 to 100° C., more preferably 40 to 60° C., still more preferably 50° C. A pH value for hydrolysis is preferably pH 3 to 9, more preferably 4 to 5.5, still more preferably pH 5. For pH adjustment, acid or alkali may be added for adjustment to a desired pH, and a buffer may be used as desired. In addition, to facilitate contact between cellulose-containing biomass and saccharifying enzyme and to uniform the concentration of sugar in hydrolysate, the hydrolysate is preferably mixed with stirring, and water is added such that the concentration of solids in cellulose is preferably 1 to 25 wt %, more preferably 5 to 20 wt %.

Step (2)

Step (2) is a step of separating the endoxylanase hydrolysate into an endoxylanase hydrolysate solid and an endoxylanase hydrolysate liquid through solid-liquid separation.

A method of solid-liquid separation is not particularly limited, and solid-liquid separation can be performed by centrifugation such as by a screw decanter; membrane separation such as by a filter press; beltpress; beltfilter; separation by spontaneous precipitation; or filtration such as by mesh screen, non-woven fabric, and filter paper.

The amount of liquid and solid separated by solid-liquid separation is not particularly limited, and the conditions therefor are preferably set such that the effect is obtained of enhancing the amount of an enzyme component recovered from the non-permeate side in Step (4) described below, and such that in performing recovery of endoxylanase and the below-mentioned recovery of xylooligosaccharide the operational conditions for solid-liquid separation of endoxylanase hydrolysate satisfy the following relational expression:

weight of endoxylanase hydrolysate solid<weight of endoxylanase hydrolysate liquid.

The hydrolysis of xylan in cellulose-containing biomass by action of endoxylanase results in production of xylooligosaccharide in the endoxylanase hydrolysate liquid. Meanwhile, cellulose is not subjected to hydrolysis by endoxylanase, and mostly is present being undegraded in the endoxylanase hydrolysate solid.

The endoxylanase hydrolysate liquid may be filtered through an ultrafiltration membrane. The endoxylanase hydrolysate liquid is filtered through an ultrafiltration membrane so that endoxylanase can be recovered on the non-permeate side of the ultrafiltration membrane and xylooligosaccharide can be recovered on the permeate side of the ultrafiltration membrane. In this case, the endoxylanase hydrolysate solid may be washed with water or brine to recover enzymes in the wash obtained, and the wash may be mixed into the endoxylanase hydrolysate liquid. The endoxylanase recovered on the non-permeate side of the ultrafiltration membrane can also be reused for hydrolysis of cellulose-containing biomass in Step (1). Since xylooligosaccharide has the effect of calming intestinal disorders, it is approved as Food for Specified Health Use and is a valuable oligosaccharide.

The ultrafiltration membrane and the filtering method used in this Step are the same as the ultrafiltration membrane and the filtering method of the filtering step in the Step (4) described below.

Step (3)

Step (3) is a step of obtaining a cellulase hydrolysate by hydrolyzing the endoxylanase hydrolysate solid using cellulase derived from a filamentous fungus.

Hydrolysis of the endoxylanase hydrolysate solid with filamentous fungus-derived cellulase seeks to lower the molecular weight of cellulose in the endoxylanase hydrolysate solid, thereby producing a monosaccharide or oligosaccharide. In the hydrolysis of the endoxylanase hydrolysate solid, mannan, arabinan, and a hemicellulose component such as the xylan that has not been completely decomposed in the hydrolysis with endoxylanase are also hydrolyzed at the same time. In this Step, filamentous fungus-derived cellulase is used as a saccharifying enzyme to hydrolyze an endoxylanase hydrolysate solid.

Filamentous fungus-derived cellulase is an enzyme composition comprising a plurality of enzyme components such as cellobiohydrolase, endoglucanase, exoglucanase, β-glucosidase, endoxylanase, and xylosidase, and has an activity to saccharify cellulose by hydrolysis. Since such a plurality of enzyme components are contained in filamentous fungus-derived cellulase, efficient hydrolysis of cellulose can be carried out by their synergistic effect or complementary effect of the plurality of enzyme components in hydrolysis of cellulose.

Examples of filamentous fungus-derived cellulase include cellulase derived from microorganisms such as *Trichoderma*, *Aspergillus*, *Cellulomonas*, *Clostridium*, *Streptomyces*, *Humicola*, *Acremonium*, *Irpex*, *Mucor*, *Talaromyces*, *Phanerochaete*, white-rot fungus, and brown decay fungus. The cellulase may also be derived from a mutant strain of such a microorganism prepared by mutagenesis using a mutagen, UV irradiation or the like to enhance the cellulase productivity. Among filamentous fungi, cellulase derived from the *Trichoderma*-derived cellulase which produces, in a culture liquid, large amounts of enzyme components having high specific activities in hydrolysis of cellulose is preferably used.

*Trichoderma*-derived cellulase is an enzyme composition whose main component is cellulase derived from a microorganism(s) belonging to the genus *Trichoderma*. *Trichoderma* microorganisms are not particularly limited and are preferably *Trichoderma reesei*, specifically including *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80, and *Trichoderma viride* QM9123.

Cellobiohydrolase is a general term for cellulase that begins hydrolysis from the end of cellulose to release cellobiose. The group of enzymes belonging to cellobiohydrolase are described as EC number: EC 3.2.1.91.

Endoglucanase is a general term for cellulase that hydrolyzes cellulose molecular chains from their central portions.

The group of enzymes belonging to endoglucanase are described as EC numbers: EC 3.2.1.4, EC 3.2.1.6, EC 3.2.1.39, and EC 3.2.1.73.

Exoglucanase is a general term for cellulase that hydrolyze cellulose molecular chains from their termini. The group of enzymes belonging to exoglucanase are described as EC numbers: EC 3.2.1.74 and EC 3.2.1.58.

β-glucosidase is a general term for cellulase that hydrolyze cellooligosaccharides or cellobiose. The group of enzymes belonging to β-glucosidase are described as EC number: EC 3.2.1.21.

Xylosidase is a general term for cellulases that act on xylooligosaccharides. The group of enzymes belonging to xylosidase are described as EC number: EC 3.2.1.37.

Enzymes contained in such filamentous fungus-derived cellulase can be separated by a known method such as gel filtration, ion exchange or two-dimensional electrophoresis, and the separated components can be subjected to determination of their amino acid sequences (by N-terminal analysis, C-terminal analysis or mass spectrometry) and identification by comparison with databases.

The enzyme activity of a filamentous fungus-derived cellulase can be evaluated based on its hydrolytic activities on polysaccharides such as the Avicel-degrading activity, xylan-degrading activity, carboxymethyl cellulose (CMC)-degrading activity, cellobiose-degrading activity, and mannan-degrading activity. The main enzymes showing the Avicel-degrading activity are cellobiohydrolase or exoglucanase, which degrade cellulose from its terminal portions. The main enzymes showing the xylan-degrading activity are xylanase and β-xylosidase. The main enzymes involved in the CMC-degrading activity are cellobiohydrolase, exoglucanase, and endoglucanase. The main enzyme showing the cellobiose-degrading activity is β-glucosidase. The term "main" herein is used to mean that the component(s) is/are involved in the degradation to the highest extent(s), while other enzyme components are also involved in the degradation.

Since filamentous fungi produce cellulase in the culture liquid, the culture liquid may be used as it is as a crude enzyme agent, or enzymes may be purified and formulated by a known method to provide a filamentous fungus-derived cellulase mixture. When filamentous fungus-derived cellulase is purified and formulated, the cellulase formulation may also contain substances other than enzymes such as a protease inhibitor, dispersant, solubilizer, and/or stabilizer.

Crude enzyme products are preferably used as filamentous fungus-derived cellulase. The crude enzyme product is derived from a culture supernatant obtained after culturing filamentous fungus for an arbitrary period in a medium prepared such that the microorganism produces cellulase. The medium components to be used therefor are not limited, and a medium supplemented with cellulose to promote production of cellulase may be generally used. As the crude enzyme product, the culture liquid may be used as it is, or a culture supernatant processed only by removal of the fungus body may be preferably used.

The weight ratios of enzyme components in the crude enzyme product are not limited and, for example, a culture liquid derived from *Trichoderma reesei* contains 50 to 95% by weight cellobiohydrolase, and also contains as other components endoglucanase, β-glucosidase and the like. Microorganisms belonging to *Trichoderma* produce strong cellulase components into the culture liquid, while the β-glucosidase activity in the culture liquid is low since β-glucosidase is retained in the cells or on the cell surfaces. Therefore, β-glucosidase from a different species or from the same species may be added to the crude enzyme product. As the β-glucosidase from a different species, β-glucosidase derived from *Aspergillus* may be preferably used. Examples of the β-glucosidase derived from *Aspergillus* include "Novozyme 188," which is commercially available from Novozyme. A method of adding, to the crude enzyme product, β-glucosidase from a different species or from the same species may be a method in which a gene may be introduced into a *Trichoderma* microorganism, the *Trichoderma* microorganism having undergone genetic recombination such that β-glucosidase is produced into the culture liquid is cultured, and the culture liquid is isolated.

The reaction conditions for hydrolysis with filamentous fungus-derived cellulase are not limited as long as it is performed according to the preferable reaction conditions of filamentous fungus-derived cellulase, while in our methods, the general reaction temperature in using filamentous fungus-derived cellulase is preferably 15 to 100° C., more preferably 40 to 60° C., still more preferably about 50° C.

As a pH value of the endoxylanase hydrolysate solid during a hydrolysis reaction, a pH value during cellulase treatment is preferably 3 to 9, more preferably 4 to 5.5, still more preferably about 5, as the effect of hydrolysis with filamentous fungus-derived cellulase is highest at an optimal pH of the filamentous fungus-derived cellulase.

Since a pH value varies in a process of hydrolysis, a pH adjustment is preferably made using acid or alkali for adjustment to a desired pH. In the pH adjustment, a buffer may also be used with the hydrolysate, as desired. Examples of acid include, for example, hydrochloric acid, sulfuric acid, nitric acid, and phosphoric acid, and sulfuric acid, nitric acid, and phosphoric acid are preferably used in view of the tendency not to cause inhibition during fermentation of the sugar liquid obtained in our methods, and more preferably sulfuric acid is used in view of economy. As alkali, ammonia, sodium hydroxide, calcium hydroxide, and solutions including them are preferably used in view of economy, more preferably ammonia and sodium hydroxide, which are monovalent ions, are used in view of suppressing the occurrence of membrane fouling during membrane separation in Step (4) described below, and still more preferably ammonia is used in view of the tendency not to cause inhibition during fermentation.

In addition, to facilitate contact between the endoxylanase hydrolysate solid and the saccharifying enzyme and to homogenize the concentration of sugar in hydrolysate, the endoxylanase hydrolysate solid and the saccharifying enzyme are preferably mixed with stirring.

Water is added such that the concentration of solid in cellulose is preferably 1 to 25 wt %, more preferably 5 to 20 wt %.

Step (4)

Step (4) is a step of filtering the cellulase hydrolysate through an ultrafiltration membrane to recover a sugar liquid from the permeate side and recover an enzyme component from the non-permeate side. The enzyme components recovered as a non-permeate can be reused in Step (3) so that the amount of the enzyme components used in Step (3) can be reduced.

An ultrafiltration membrane allows permeation of glucose (molecular weight, 180) and xylose (molecular weight, 150), which are monosaccharides, and the one having a molecular weight cutoff which can block filamentous fungus-derived cellulase can be used. The molecular weight cutoff of the ultrafiltration membrane may be 500 to 50,000, and from the viewpoint of separating impurities that show inhibitory actions against the enzymatic reaction from the enzyme, the molecular weight cutoff is more preferably 5,000 to 50,000, still more preferably 10,000 to 30,000.

Since the pore size of an ultrafiltration membrane is too small, measurement of the pore size on its membrane surface is difficult even under the electron microscope or the like and, therefore, a value called the molecular weight cutoff is used as an index of the pore size instead of the average pore size. A molecular weight cutoff refers to a molecular weight relative to which the blocking rate is 90% when plotting the molecular weight data of the solute along the abscissa and the blocking rate data along the ordinate.

Examples of the material of the ultrafiltration membrane include polyether sulfone (PES), polysulfone (PS), polyacrylonitrile (PAN), polyvinylidene fluoride (PVDF), regenerated cellulose, cellulose, cellulose ester, sulfonated polysulfone, sulfonated polyether sulfone, polyolefin, polyvinyl alcohol, polymethyl methacrylate, and polytetrafluoroethylene. As an ultrafiltration membrane material used, an ultrafiltration membrane using a synthetic polymer material such as PES or PVDF is preferably used since regenerated cellulose, cellulose, and cellulose ester undergo degradation by cellulase.

Examples of the method of filtration through the ultrafiltration membrane include dead-end filtration and cross-flow filtration, and the method is preferably cross-flow filtration in view of suppression of membrane fouling.

Examples of the form of the ultrafiltration membrane which may be used as appropriate include the flat membrane, spiral-wound membrane, tubular membrane and hollow fiber membrane. Specific examples of the ultrafiltration membrane include Type G-5, Type G-10, Type G-20, Type G-50, Type PW, and Type HWSUF, manufactured by DESAL; HFM-180, HFM-183, HFM-251, HFM-300, HFK-131, HFK-328, MPT-U20, MPS-U20P, and MPS-U20S, manufactured by KOCH; SPE1, SPE3, SPE5, SPE10, SPE30, SPV5, SPV50, and SOW30, manufactured by Synder; products of Microza (registered trademark) UF series, manufactured by Asahi Kasei Corporation, having molecular weight cutoffs of 3,000 to 10,000; and NTR7410 and NTR7450, manufactured by Nitto Denko Corporation.

As a method of filtration, filter pressing, vacuum filtration, centrifugal filtration, and the like are preferably used. Examples of a filtration operation include constant pressure filtration, constant flow filtration, non-constant pressure and non-constant flow filtration, and the like. The filtration operation may be a multistage filtration using the above-mentioned ultrafiltration membrane two or more times.

Since the non-permeate recovered in Step (4) contains filamentous fungus-derived cellulase as an enzyme component, it can be used as the filamentous fungus-derived cellulase of Step (3) by mixing the recovered non-permeate containing filamentous fungus-derived cellulase into the filamentous fungus-derived cellulase used in Step (3). This allows reduction of the amount of filamentous fungus-derived cellulase newly used in Step (3) and allows an attempt to reduce the cost for filamentous fungus-derived cellulase.

Thus, according to our method of producing a sugar liquid, an endoxylanase hydrolysate solid is produced by solid-liquid separation of the endoxylanase hydrolysate obtained by hydrolysis of cellulose-containing biomass with endoxylanase prior to a saccharification reaction of the cellulose-containing biomass. Recovering and reusing the non-permeate obtained by hydrolysis of this endoxylanase hydrolysate solid with a filamentous fungus-derived cellulase can further enhance the effect of reduction in the amount of filamentous fungus-derived cellulase, which is a saccharifying enzyme, used in production processes of a sugar liquid. In addition, by filtering the endoxylanase hydrolysate liquid obtained by solid-liquid separation of the endoxylanase hydrolysate, xylooligosaccharide can be recovered and endoxylanase can be recovered as well. The obtained endoxylanase can be reused for hydrolysis of cellulose-containing biomass and, hence, a sugar liquid can be produced while reducing the amount of endoxylanase used for hydrolysis of cellulose-containing biomass, especially a hemicellulose component. Therefore, our method of producing a sugar liquid allows production of a sugar liquid while recovering and reusing a saccharifying enzyme and allows keeping the production costs of a sugar liquid low.

Other Variations

Figure 2:
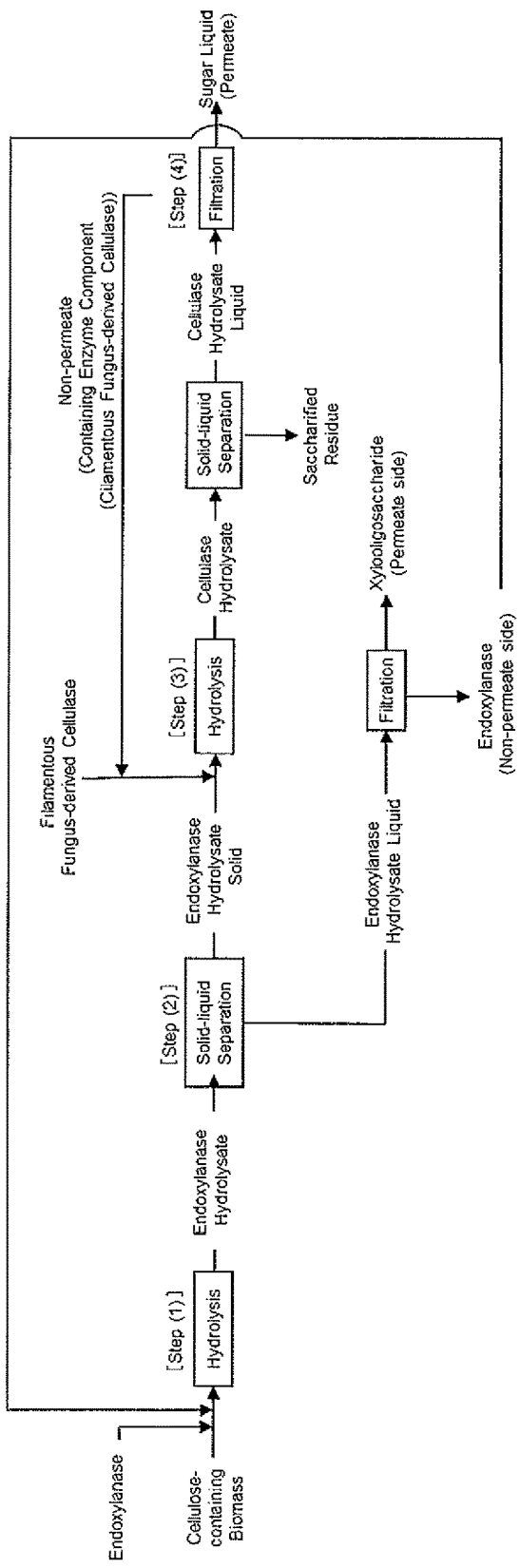
FIG. 2 is a view showing another example of our method of producing a sugar liquid.

Our methods have been described with reference to, but are not limited to, when the non-permeate obtained by filtration of cellulase hydrolysate in Step (4) is mixed with the filamentous fungus-derived cellulase of Step (3). Another example of the method of producing a sugar liquid is shown in FIG. 2. As shown in FIG. 2, for example, the cellulase hydrolysate obtained in Step (3) is subjected to solid-liquid separation and separated into a solution containing a sugar (cellulase hydrolysate liquid) and a saccharified residue which is a solid. The obtained cellulase hydrolysate liquid is filtered through an ultrafiltration membrane in Step (4) and separated into a non-permeate containing filamentous fungus-derived cellulase and a sugar liquid which is a permeate. This results in recovery of a non-permeate containing filamentous fungus-derived cellulase and recovery of a sugar liquid as a permeate. The recovered non-permeate can be reused and mixed into the filamentous fungus-derived cellulase used in Step (3). Thus, by removing solids from the cellulase hydrolysate through the previous solid-liquid separation of the cellulase hydrolysate, the filamentous fungus-derived cellulase contained in the cellulase hydrolysate can be efficiently recovered therefrom in Step (4). This allows production of a sugar liquid while enhancing the recovery rate of the filamentous fungus-derived cellulase.

In a method of solid-liquid separation, as in Step (2), solid-liquid separation can be performed by centrifugation such as by a screw decanter; membrane separation such as by a filter press; beltpress; beltfilter; separation by spontaneous precipitation; or filtration such as by mesh screen, non-woven fabric, and filter paper. Among these, a filtration method such as a screw decanter, filter press, and beltpress is preferably used. Using these methods of filtration, a solution component having less insoluble solid and less suspended matter can be obtained. A smaller amount of suspended matter is preferable because it suppresses the fouling of the ultrafiltration membrane in Step (4).

It is also preferable to filter, additionally through a microfiltration membrane, the cellulase hydrolysate liquid obtained by solid-liquid separation. By filtering the cellulase hydrolysate liquid through a microfiltration membrane, solids which have not been completely separated by solid-liquid separation can be removed and, hence, the filamentous fungus-derived cellulase contained in the cellulase hydrolysate can be further efficiently recovered therefrom in Step (4).

A microfiltration membrane refers to a membrane having the average pore size of 0.01 μm to 5 mm. Examples of the material of the ultrafiltration membrane are not particularly limited as long as it removes solids that have not been completely separated through the above-mentioned solid-liquid separation, and include organic materials such as cellulose, cellulose ester, polysulfone, polyether sulfone, chlorinated polyethylene, polypropylene, polyolefin, polyvinyl alcohol, polymethyl methacrylate, polyvinylidene fluoride, polytetrafluoroethylene; metals such as stainless steel; and inorganic materials such as ceramics.

As described above, the obtained sugar liquid can be used for various applications of fermentation feedstocks and the like such as food products materials, pharmaceuticals materials, and chemical products. The obtained sugar liquid can be used as fermentation feedstocks to grow microorganisms having the ability to produce chemical products, thereby allowing various chemical products to be manufactured. To grow microorganisms means that sugar components or amino sources contained in a sugar liquid are used as nutrients for microorganisms to cause the proliferation and growth continuation of the microorganisms. Specific examples of the chemical products include alcohols, organic acids, amino acids, and nucleic acids, which are substances mass-produced in the fermentation industry. Such chemical products are produced and accumulated inside and outside the living body as a result of metabolism using sugar components in the sugar liquid as carbon sources. Examples of the chemical products that can be produced by microorganisms include alcohols such as ethanol, propanol, butanol, 1,3-propanediol, 1,4-butanediol, and glycerol; organic acids such as acetic acid, lactic acid, pyruvic acid, succinic acid, malic acid, itaconic acid, and citric acid; nucleosides such as inosine and guanosine; and amine compounds such as cadaverine. Further, the sugar liquid obtained by the method of producing a sugar liquid can be applied to production of enzymes, antibiotics, recombinant proteins, and the like. The microorganisms used for production of such chemical products are not limited as long as the microorganisms are capable of efficiently producing the chemical products of interest, and examples of the microorganisms that may be used include microorganisms such as *E. coli*, yeasts, filamentous fungi, and *Basidiomycetes*.

EXAMPLES

By way of Examples, our methods are concretely described below. However, this disclosure is not limited to thereto.

Reference Example 1: Preparation of Filamentous Fungus-Derived Cellulase (Culture Liquid)

Filamentous fungus-derived cellulase (culture liquid) was prepared by the following method.
Preculture
The mixture of 5% (w/vol) corn steep liquor, 2% (w/vol) glucose, 0.37% (w/vol) ammonium tartrate, 0.14 (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid, and 0.0026% (w/vol) hexaammonium heptamolybdate tetrahydrate added to distilled water was prepared, and 100 mL of this distilled water including the above-mentioned components was placed in a baffled 500-mL Erlenmeyer flask, followed by sterilization by autoclaving at a temperature of 121° C. for 15 minutes. After allowing the mixture to cool, PE-M and Tween 80, each of which was sterilized by autoclaving at a temperature of 121° C. for 15 minutes separately from the mixture, were added to the above-mentioned baffled 500-mL Erlenmeyer flask at 0.01% (w/vol) each. To this preculture medium, *Trichoderma reesei* ATCC66589 was inoculated at 1×10⁵ cells/mL, and the cells were cultured at a temperature of 28° C. for 72 hours with shaking at 180 rpm, using a shaker (BIO-SHAKER BR-40LF manufactured by TAITEC CORPORATION) to provide a preculture liquid.
Main Culture
The mixture of 5% (w/vol) corn steep liquor, 2% (w/vol) glucose, 10% (w/vol) cellulose (Avicel), 0.37% (w/vol) ammonium tartrate, 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid, and 0.0026% (w/vol) hexaammonium heptamolybdate tetrahydrate added to distilled water was prepared, and 2.5 L of this distilled water including the above-mentioned components was placed in a 5 L capacity stirring jar (DPC-2A, ABLE Corporation) container, followed by sterilization by autoclaving at a temperature of 121° C. for 15 minutes. After allowing the mixture to cool, PE-M and Tween 80, each of which was sterilized by autoclaving at a temperature of 121° C. for 15 minutes separately from the mixture, were added to the mixture at 0.1% (w/v) each. To the resulting mixture, 250 mL of the *Trichoderma reesei* ATCC66589 precultured in the liquid culture medium by the above method was inoculated. The cells were then cultured with shaking under the conditions at a temperature of 28° C. at 300 rpm at an aeration rate of 1 vvm for 87 hours, and were centrifuged. After this, the supernatant was filtered through a membrane (Stericup-GV, PVDF material, from Millipore). This culture liquid adjusted under the above-mentioned conditions was used as filamentous fungus-derived cellulase in the Examples below.

Reference Example 2: Method of Measuring Filamentous Fungus-Derived Cellulase Activity For the enzyme activity of filamentous fungus-derived cellulase as the activity of the group of enzymes involved in the degradation of cellulose, (1) the degrading activity for 4-nitro-phenyl-β-D-lactopyranoside (pNP-Lac) as the activity of cellobiohydrolase and endoglucanase, (2) the degrading activity for 4-nitrophenyl-β-D-glucopyranoside (pNP-Glc) as the activity of βglucosidase, and (3) the degrading activity for 4-nitrophenyl-β-D-xylopyranoside (pNP-Xyl) as the activity of endoxylanase and xylosidase involved in the degradation of xylan which is the main component of hemicellulose were each measured and evaluated by the following procedures. The substrates of (1) to (3) described above are collectively referred to as the pNP-sugar.

To 0.9 mL of 100 mM acetic acid buffer (pH 5.0) containing each substrate at a concentration of 1 mM each, 0.1 mL of the enzyme liquid was added and reacted at 30° C. The reaction time was 60 minutes for the substrate of pNP-Lac, 10 minutes for pNP-Glc, and 30 minutes for pNP-Xyl, after which reaction, 0.1 mL of 2 M sodium carbonate aqueous solution was added to stop the reaction, and absorbance at 405 nm was measured (ODtest). As a blank test, the substrate solution to which a 2 M sodium carbonate aqueous solution and an enzyme solution were added in this order was measured for absorbance at 405 nm in the same way (ODblank). The amount of enzyme that produces 1 μmol of 4-nitrophenol per minute in the above reaction system was defined as 1 U, and the activity value (U/mL) was calculated according to the following equation. The millimole molecular extinction coefficient of 4-nitrophenol in the above reaction system was 17.2 L/mmol/cm.

pNP-Lac degrading activity (U/mL)={(ODtest−ODblank)×1.1 (mL)×enzyme dilution ratio}/{17.2×60 (minutes)×0.1 (mL)} pNP-Glc degrading activity (U/mL)={(ODtest−ODblank)×1.1 (mL)×enzyme dilution ratio}/{17.2×10 (minutes)×0.1 (mL)} pNP-Xyl degrading activity (U/mL)={(ODtest−ODblank)×1.1 (mL)×enzyme dilution ratio}/{17.2×60 (minutes)×0.1 (mL)}

Reference Example 3: Preparation of Cellulose-Containing Biomass

With 100 g by dry weight of bagasse, 9.3 g of caustic soda was mixed and reacted at 121° C. for 30 minutes to prepare an alkali-treated bagasse.

Reference Example 4: Preparation of Purified Acremonium-Derived Endoxylanase

"Acremonium cellulase" commercially available from Meiji Seika Pharma Co., Ltd. was purified by the below-mentioned procedures to obtain an enzyme, which was the purified Acremonium-derived endoxylanase.
Preparation of Fraction 1, 2
1) The strongly basic anion exchange chromatography: QAE-Toyopearl 550C (Tosoh Corporation) was used to adsorb the crude enzyme and fractionate a xylanase-active fraction eluted with an acetic acid buffer (0.02 M, pH 5.5).
2) The weakly basic anion exchange chromatography: DEAE-Toyopearl 650S (Tosoh Corporation) was used to adsorb the fractionated fraction of 1) above with a 0.02 M acetic acid buffer (pH 6.0) and fractionate a xylanase-active fraction eluted with an acetic acid buffer (0.02 M, pH 5.5).
3) The strongly basic anion exchange chromatography: Mono S (Pharmacia Corporation) was used to adsorb the fractionated fraction of 2) above with an acetic acid buffer (0.1 M, pH 3.5), followed by linear gradient elution with an acetic acid buffer (0.1 M, pH 3.5) including 0 to 0.05 M NaCl, to fractionate a fraction showing a xylanase activity. Two fractions (Fraction 1, Fraction 2) showing only a xylanase activity were recovered.
Preparation of Fraction 3, 4, 5
4) The gel filtration chromatography: Superdex 75 (Pharmacia Corporation) was allowed to pass the fractionated Fraction 1 of 3) above therethrough using an acetic acid buffer (0.05 M, pH 3.5) containing 0.1 M NaCl, to fractionate a xylanase-active fraction (Fraction 3).
5) The gel filtration chromatography: Superdex 75 (Pharmacia Corporation) was allowed to pass Fraction 2 of 3) above therethrough using an acetic acid buffer (0.05 M, pH 3.5) containing 0.1 M NaCl, to fractionate two xylanase-active fractions (Fraction 4, Fraction 5).

By the above-mentioned procedures, Fraction 3, Fraction 4, and Fraction 5 were highly purified until they show a single protein-stained band on SDS-polyacrylamide gel electrophoresis. A mixture of Fraction 3, Fraction 4, and Fraction 5 was rendered the purified endoxylanase. After a reaction under a substrate of Birchwood xylan at 50° C. at pH 5 for 10 minutes, the dinitrosalicylic acid method (DNS method) was used to measure absorbance at 540 nm, thereby measuring the amount of a reducing sugar contained in a reaction liquid resulting from the reaction, and the activity of the endoxylanase was 100 U/mg.

Reference Example 5: Measurement of Sugar Concentration

The concentration of each of glucose and xylose contained in the sugar liquid was quantified relative to an authentic preparation by high performance liquid chromatography (HPLC conditions) described below.
(HPLC Conditions)
Column: Shodex SH1011 (Showa Denko K.K.)
Mobile phase: 5 mM sulfuric acid (flow: 0.6 mL/min.)
Reaction liquid: none
Detection method: RI (refractive index)
Temperature: 65° C.

Example 1: Use of Endoxylanase Derived from Microorganisms of the Acremonium Genus Step (1)
To 1 g of the alkali-treated bagasse adjusted in Reference Example 3, 19 g of water was added to make an adjustment such that the concentration of the solids was 5%. To the prepared cellulose-containing biomass, endoxylanase derived from microorganisms of the Acremonium genus prepared in Reference Example 4 was added to perform hydrolysis. The pretreated endoxylanase derived from microorganisms of the Acremonium genus was added in an addition amount of 0.1 mg/g and adjusted to be pH 5 with a hydrochloric acid, followed by endoxylanase hydrolysis. The endoxylanase hydrolysis reaction was performed at 50° C. for 24 hours.
Step (2)
After the endoxylanase reaction, 10 g of endoxylanase hydrolysate liquid and 10 g of endoxylanase hydrolysate solid were recovered through solid-liquid separation with a 12 mesh stainless steel sieve.
Step (3)
To 10 g of the solid (10% concentration of solid) from solid-liquid separation, the filamentous fungus-derived cellulase prepared in Reference Example 1 was added to perform hydrolysis. The pretreated filamentous fungus-derived cellulase was added in an addition amount of 8 mg/g and adjusted to be pH 5 with a hydrochloric acid, followed by initiation of hydrolysis. The hydrolysis was performed at 50° C. for 24 hours.
Step (4)
After cellulase saccharification, cellulase hydrolysate solid and cellulase hydrolysate liquid were separated through solid-liquid separation by centrifugation (4500G, 10 minutes). Further, the cellulase hydrolysate liquid was filtered through a membrane (Stericup-GP, PES material, manufactured by Millipore), and the resulting supernatant was centrifuged at 4500G using an ultrafiltration membrane with a molecular weight cutoff of 10,000 (VIVASPIN 20, PES material, manufactured by Sartorius stedim biotech) until the non-permeate side of the ultrafiltration membrane became 1 mL. To the membrane fraction, 10 mL of distilled water was added; the mixture was again centrifuged at 4500G until the fraction on the non-permeate side became 1 mL, to give the recovered enzyme; the enzyme activity was measured by the method as in Reference Example 2; and a relative value was determined with the activity of 100 for the added enzyme.

Example 2: Use of Endoxylanase Derived from Microorganisms of the Aspergillus Genus Step (1)
To 1 g of the alkali-treated bagasse adjusted in Reference Example 3, 19 g of water was added to make an adjustment such that the concentration of the solids was 5%. To the prepared cellulose-containing biomass, endoxylanase derived from microorganisms of the *Aspergillus* genus (80 U/mg activity, manufactured by Megazyme) was added to perform hydrolysis. The pretreated endoxylanase derived from microorganisms of the *Aspergillus* genus was added in an addition amount of 0.13 mg/g and adjusted to be pH 5 with a hydrochloric acid, followed by endoxylanase hydrolysis. The endoxylanase hydrolysis reaction was performed at 50° C. for 24 hours.

Step (2)

After the endoxylanase reaction, 10 g of endoxylanase hydrolysate liquid and 10 g of endoxylanase hydrolysate solid were recovered through solid-liquid separation with a 12 mesh stainless steel sieve.

Step (3)

To 10 g of the solid from solid-liquid separation, the filamentous fungus-derived cellulase prepared in Reference Example 1 was added to perform hydrolysis. The hydrolysis by cellulase was performed in the same manner as in Comparative Example 1.

Step (4)

This step was performed in the same manner as in Example 1.

Example 3: Recovery of Endoxylanase of Step (2) in Example 1 and Recovery of Xylooligosaccharide Step (1), Step (2), Step (3) and Step (4) were performed in the same manner as in Example 1. The endoxylanase hydrolysate liquid obtained in Step (2) was filtered through a membrane (Stericup-GP, PES material, manufactured by Millipore), and the resulting supernatant was centrifuged at 4500G using an ultrafiltration membrane with a molecular weight cutoff of 10,000 (VIVASPIN 20, PES material, manufactured by Sartorius stedim biotech) until the non-permeate side of the ultrafiltration membrane became 1 mL. To the membrane fraction, 10 mL of distilled water was added; the mixture was again centrifuged at 4500G until the fraction on the non-permeate side became 1 mL, to give the recovered endoxylanase enzyme; after a reaction under a substrate of Birchwood xylan at 50° C. at pH 5 for 10 minutes, the dinitrosalicylic acid method (DNS method) was used to measure absorbance at 540 nm, based on which a relative value of the recovered endoxylanase with the activity of 100 for the added endoxylanase was determined as the recovery ratio of the endoxylanase. The recovery ratio of the endoxylanase was 73%. The concentration of xylooligosaccharide in the permeate of the endoxylanase hydrolysate liquid was measured according to Reference Example 5 to find that 80 mg of the xylooligosaccharide per g by weight of alkali-treated bagasse was recovered.

Comparative Example 1: Omission of Step (1) and Step (2) in Example 1

To 1 g of the cellulose-containing biomass adjusted in Reference Example 3, 9 g of water was added and prepared such that the concentration of the solids was 10%. To the prepared cellulose-containing biomass, the filamentous fungus-derived cellulase prepared in Reference Example 1 was added to perform hydrolysis. The conditions for hydrolysis were the same as in Example 1. From the obtained hydrolysate, the enzyme was recovered according to Step (4) in Example 1, and the enzyme activity was measured by the method in Reference Example 2.

Comparative Example 2: Omission of Step (1) in Example 1

To 1 g of the cellulose-containing biomass adjusted in Reference Example 3, 19 g of water was added and adjusted such that the concentration of the solids was 5%. Through solid-liquid separation of this with a 12 mesh stainless steel sieve, 10 g of the liquid side and 10 g of the solid side were recovered. To 10 g of the solid from solid-liquid separation, the filamentous fungus-derived cellulase prepared in Reference Example 1 was added to perform hydrolysis according to Step (3) in Example 1. From the obtained hydrolysate, the enzyme was recovered according to Step (4) in Example 1, and the enzyme activity was measured by the method in Reference Example 2.

Comparative Example 3: Omission of Step (2) in Example 1

To 1 g of the cellulose-containing biomass adjusted in Reference Example 3, 9 g of water was added and adjusted such that the concentration of the solids was 10%. To the prepared cellulose-containing biomass, the endoxylanase derived from microorganisms of the *Acremonium* genus prepared in Reference Example 4 was added to perform hydrolysis. The pretreated endoxylanase derived from microorganisms of the *Acremonium* genus was added in an addition amount of 0.1 mg/g and adjusted to be pH 5 with a hydrochloric acid, followed by endoxylanase hydrolysis. The endoxylanase hydrolysis reaction was performed at 50° C. for 24 hours. After the endoxylanase reaction, solid-liquid separation was not performed, and the filamentous fungus-derived cellulase prepared in Reference Example 1 was added, followed by hydrolysis according to Step (3) in Example 1. From the obtained hydrolysate, the enzyme was recovered according to Step (4) in Example 1, and the enzyme activity was measured by the method in Reference Example 2.

Comparative Example 4: Use of Endoxylanase Derived from Microorganisms of the *Trichoderma* Genus To 1 g of the cellulose-containing biomass adjusted in Reference Example 3, 19 g of water was added and adjusted such that the concentration of the solids was 5%. To the prepared cellulose-containing biomass, 0.04 mg/g of the pretreated endoxylanase derived from the *Trichoderma viride* (250 U/mg activity, manufactured by Megazyme) was added and adjusted to be pH 5 with hydrochloric acid, followed by endoxylanase hydrolysis. The endoxylanase hydrolysis reaction was performed at 50° C. for 24 hours. After the endoxylanase reaction, 10 g of endoxylanase hydrolysate liquid and 10 g of endoxylanase hydrolysate solid were recovered through solid-liquid separation with a 12 mesh stainless steel sieve. To 10 g of the solid from solid-liquid separation, the filamentous fungus-derived cellulase prepared in Reference Example 1 was added, followed by hydrolysis according to Step (3) in Example 1. From the obtained hydrolysate, the enzyme was recovered according to Step (4) in Example 1, and the enzyme activity was measured by the method in Reference Example 2.

Table 1 summarizes the results of the recovery ratios of the enzymes in Comparative Examples 1 to 4 and Examples 1 and 2. As can be seen in Table 1, the pNP-Lac, pNP-Glc, and pNP-Xyl degrading activities of the recovered enzymes are high in Examples 1 and 2 with the enhanced enzyme recovery ratios, compared with Comparative Examples 1 to 4.

In Comparative Example 3, the endoxylanase derived from microorganisms of the *Acremonium* genus was used in Step (1) but the activity of the recovered cellulase was not enhanced without performing Step (2), and this made it obvious that the solid-liquid separation in Step (2) is needed to obtain the desired effect.

Comparative Example 4 is an example in which xylanase derived from microorganisms of the *Trichoderma* genus was used in Step (1). WO '040 indicates that hydrolysis with only the recovered enzyme is performed prior to hydrolysis with filamentous fungus-derived cellulase, that xylosidase which converts endoxylanase and xylobiose to xylose is accumulated in the recovered cellulase, and that the cellulase activity of the recovered enzyme and the saccharification ratio in the cellulase hydrolysis are enhanced. The same effect as described in WO '040 was expected, but compared with Examples 1 and 2, the recovery ratio of cellulase was lower, and compared with Comparative Example 1, the recovery ratio of cellulase was enhanced only slightly.

TABLE 1

Enzyme Activity of Recovered Enzyme Components Recovered from Cellulase Hydrolysate Using Ultrafiltration Membrane

| | Endoxylanase in Step (1) derived from: | Carrying out Step (2) | Enzyme Recovery Ratio (%) | | |
|---|---|---|---|---|---|
| | | | pNP-Lac | pNP-Glc | pNP-Xyl |
| Example 1 | *Acremonium* Genus | Yes | 85 | 80 | 45 |
| Example 2 | *Aspergillus* Genus | Yes | 65 | 70 | 15 |
| Comparative Example 1 | Step (1) not performed | No | 50 | 45 | 5 |
| Comparative Example 2 | Step (1) not performed | Yes | 50 | 45 | 4 |
| Comparative Example 3 | *Acremonium* Genus | No | 55 | 50 | 6 |
| Comparative Example 4 | *Trichoderma* Genus | Yes | 56 | 55 | 7 |

The invention claimed is:

1. A method of producing a sugar liquid from a cellulose-containing biomass, comprising:
    Step (1): obtaining an endoxylanase hydrolysate by hydrolyzing the cellulose-containing biomass using an endoxylanase derived from microorganisms of the *Acremonium* genus or the *Aspergillus* genus,
    Step (2): separating the endoxylanase hydrolysate into an endoxylanase hydrolysate solid and an endoxylanase hydrolysate liquid through solid-liquid separation,
    Step (3): obtaining a cellulase hydrolysate by hydrolyzing the endoxylanase hydrolysate solid using cellulase derived from a filamentous fungus, and
    Step (4): filtering the cellulase hydrolysate through an ultrafiltration membrane to recover a sugar liquid from the permeate side and recover an enzyme component from the non-permeate side.

2. The method according to claim 1, wherein the cellulose-containing biomass is pretreated by one or more methods selected from the group consisting of alkali treatment, hydrothermal treatment, and dilute sulfuric acid treatment.

3. The method according to claim 1, wherein the activity of the endoxylanase is 80 U/mg-protein or more.

4. The method according to claim 1, wherein the solid-liquid separation of the endoxylanase hydrolysate satisfies the relational expression:

weight of endoxylanase hydrolysate solid<weight of endoxylanase hydrolysate liquid.

5. The method according to claim 1, further comprising filtering the endoxylanase hydrolysate liquid through an ultrafiltration membrane to recover a xylooligosaccharide liquid from the permeate side and recover an endoxylanase from the non-permeate side.

6. The method according to claim 1, wherein the filamentous fungus-derived cellulase is derived from a microorganism(s) belonging to the genus *Trichoderma*.

7. The method according to claim 1, wherein the cellulase hydrolysate filtered through the ultrafiltration membrane in Step (4) is a cellulase hydrolysate liquid obtained by solid-liquid separation of the cellulase hydrolysate.

8. The method according to claim 1, wherein the enzyme component is used as the filamentous fungus-derived cellulase in Step (3).

9. The method according to claim 2, wherein an enzyme activity of the endoxylanase is 80 U/mg-protein or more.

10. The method according to claim 2, wherein the solid-liquid separation of the endoxylanase hydrolysate satisfies the relational expression:

weight of endoxylanase hydrolysate solid<weight of endoxylanase hydrolysate liquid.

11. The method according to claim 3, wherein the solid-liquid separation of the endoxylanase hydrolysate satisfies the relational expression:

weight of endoxylanase hydrolysate solid<weight of endoxylanase hydrolysate liquid.

12. The method according to claim 2, further comprising filtering the endoxylanase hydrolysate liquid through an ultrafiltration membrane to recover a xylooligosaccharide liquid from the permeate side and recover an endoxylanase from the non-permeate side.

13. The method according to claim 3, further comprising filtering the endoxylanase hydrolysate liquid through an ultrafiltration membrane to recover a xylooligosaccharide liquid from the permeate side and recover an endoxylanase from the non-permeate side.

14. The method according to claim 4, further comprising filtering the endoxylanase hydrolysate liquid through an ultrafiltration membrane to recover a xylooligosaccharide liquid from the permeate side and recover an endoxylanase from the non-permeate side.

15. The method according to claim 2, wherein the filamentous fungus-derived cellulase is derived from a microorganism(s) belonging to the genus *Trichoderma*.

16. The method according to claim 3, wherein the filamentous fungus-derived cellulase is derived from a microorganism(s) belonging to the genus *Trichoderma*.

17. The method according to claim 4, wherein the filamentous fungus-derived cellulase is derived from a microorganism(s) belonging to the genus *Trichoderma*.

18. The method according to claim 5, wherein the filamentous fungus-derived cellulase is derived from a microorganism(s) belonging to the genus *Trichoderma*.

19. The method according to claim 2, wherein the cellulase hydrolysate filtered through the ultrafiltration membrane in Step (4) is a cellulase hydrolysate liquid obtained by solid-liquid separation of the cellulase hydrolysate.

20. The method according to claim 3, wherein the cellulase hydrolysate filtered through the ultrafiltration membrane in Step (4) is a cellulase hydrolysate liquid obtained by solid-liquid separation of the cellulase hydrolysate.

\* \* \* \* \*